United States Patent
Sela et al.

(10) Patent No.: US 11,103,458 B2
(45) Date of Patent: Aug. 31, 2021

(54) STIMULANT ABUSE-DETERRENT COMPOSITIONS

(71) Applicant: 4P-Pharma, Lille (FR)

(72) Inventors: Yoram Sela, Raanana (IL); Itschak Lamensdorf, Modiin (IL)

(73) Assignee: 4P-Pharma, Lille (FR)

( * ) Notice: Subject to any disclaimer, the term of this patent is extended or adjusted under 35 U.S.C. 154(b) by 0 days.

(21) Appl. No.: 15/572,951

(22) PCT Filed: May 11, 2016

(86) PCT No.: PCT/IB2016/000688
§ 371 (c)(1),
(2) Date: Nov. 9, 2017

(87) PCT Pub. No.: WO2016/181218
PCT Pub. Date: Nov. 17, 2016

(65) Prior Publication Data
US 2018/0116961 A1    May 3, 2018

Related U.S. Application Data (60) Provisional application No. 62/160,627, filed on May 13, 2015.

(51) Int. Cl.
| | |
|---|---|
| *A61K 9/16* | (2006.01) |
| *A61K 31/485* | (2006.01) |
| *A61K 31/4458* | (2006.01) |
| *A61K 9/28* | (2006.01) |
| *A61K 9/50* | (2006.01) |
| *A61K 9/00* | (2006.01) |
| *A61K 9/48* | (2006.01) |
| *A61P 25/00* | (2006.01) |
| *C07D 221/18* | (2006.01) |
| *C07D 211/34* | (2006.01) |
| *A61K 45/06* | (2006.01) |
| *A61K 31/137* | (2006.01) |
| *A61K 31/473* | (2006.01) |
| *C07D 401/06* | (2006.01) |
| *A61K 36/74* | (2006.01) |
| *A61K 31/4535* | (2006.01) |
| *C07D 409/06* | (2006.01) |
| *A61K 31/445* | (2006.01) |
| *A61K 31/165* | (2006.01) |
| *C07D 489/02* | (2006.01) |
| *A61K 31/454* | (2006.01) |
| *A61K 31/4468* | (2006.01) |

(52) U.S. Cl.
CPC .......... *A61K 9/1676* (2013.01); *A61K 9/0002* (2013.01); *A61K 9/0053* (2013.01); *A61K 9/1623* (2013.01); *A61K 9/2886* (2013.01); *A61K 9/4808* (2013.01); *A61K 9/4858* (2013.01); *A61K 9/5078* (2013.01); *A61K 9/5084* (2013.01); *A61K 31/137* (2013.01); *A61K 31/165* (2013.01); *A61K 31/445* (2013.01); *A61K 31/4458* (2013.01); *A61K 31/4468* (2013.01); *A61K 31/454* (2013.01); *A61K 31/4535* (2013.01); *A61K 31/473* (2013.01); *A61K 31/485* (2013.01); *A61K 36/74* (2013.01); *A61K 45/06* (2013.01); *A61P 25/00* (2018.01); *C07D 211/34* (2013.01); *C07D 221/18* (2013.01); *C07D 401/06* (2013.01); *C07D 409/06* (2013.01); *C07D 489/02* (2013.01); *A61K 2300/00* (2013.01)

(58) Field of Classification Search
CPC .............. A61K 2300/00; A61K 31/137; A61K 31/165; A61K 31/445; A61K 31/4458; A61K 31/4468; A61K 31/4535; A61K 31/454; A61K 31/473; A61K 31/485; A61K 36/74; A61K 45/06; A61K 9/0002; A61K 9/0053; A61K 9/1623; A61K 9/1676; A61K 9/2886; A61K 9/4808; A61K 9/4858; A61K 9/5078; A61K 9/5084; A61P 25/00; C07D 211/34; C07D 221/18; C07D 401/06; C07D 409/06; C07D 489/02
See application file for complete search history.

(56) References Cited

U.S. PATENT DOCUMENTS

| | | | | |
|---|---|---|---|---|
| 2003/0170181 | A1* | 9/2003 | Midha | A61K 9/4808 424/10.4 |
| 2005/0186139 | A1* | 8/2005 | Bartholomaus | A61K 9/0004 424/10.2 |
| 2008/0318905 | A1 | 12/2008 | Muhammad et al. | |
| 2009/0221621 | A1* | 9/2009 | Sathyan | A61K 9/0004 514/282 |
| 2016/0022591 | A1* | 1/2016 | Kirsch | A61K 9/2081 424/465 |

FOREIGN PATENT DOCUMENTS

| | | | | |
|---|---|---|---|---|
| WO | 2008/027442 | A2 | 3/2008 | |
| WO | WO-2008027442 | A2 * | 3/2008 | ........... A61K 9/1635 |

OTHER PUBLICATIONS

International Search Report and Written Opinion from International Application No. PCT/IB2016/00688 dated Oct. 13, 2016.

* cited by examiner

*Primary Examiner* — Michael B. Pallay
(74) *Attorney, Agent, or Firm* — Greenberg Traurig, LLP (57) ABSTRACT

The present invention provides an abuse deterrent oral fixed-dose composition, comprising a stimulant or opioid and an abuse deterrent active, wherein the abuse deterrent active is configured to be bioavailable only when the composition is crushed, ground or dissolved.

13 Claims, 4 Drawing Sheets

STIMULANT ABUSE-DETERRENT COMPOSITIONS

CROSS REFERENCE TO RELATED APPLICATIONS

This application is a U.S. National Phase application under 35 U.S.C. 371 of International Application No. PCT/IB2016/000688, filed May 11, 2016, which claims priority to and the benefit of U.S. Provisional Patent Application Ser. No. 62/160,627, filed on May 13, 2015, the entire contents of each of which are hereby incorporated by reference in its entirety.

FIELD OF THE INVENTION

The present invention discloses novel fixed-dose combinations comprising a stimulant or opioid and an additional active acting as abuse deterrent.

BACKGROUND

Drugs containing stimulants or opioids are often abused for non-prescription uses, and this has turned into a very severe problem.

Stimulants (also known as psychostimulants or analeptics) are psychoactive drugs which are widely used for inducing temporary improvements in the mental or physical function in patients, and are available on prescription.

This class of drugs includes actives like methylphenidate (Ritalin, Concerta, Metadate or Methylin), amphetamine, metamphetamine, dexmethylphenidate, methylphenidate derivatives amphetamine, modafinil (Provigil) etc., or their mixtures. The positive effects of these stimulants include, for example, enhanced alertness, wakefulness, productivity and motivation. The Ritalin that is abused in the United States typically is diverted from legitimate sources. In some cases abusers obtain the drug from peers, friends, or family members. Often, individuals who have legitimate prescriptions sell or give away their supply. Ritalin also is acquired through theft from individuals with legitimate prescriptions or from school medicine dispensaries.

Abuse of Ritalin typically is associated with young people, such as, for example, preadolescents, teenagers, or young adults. The increased use of the drug for treatment of ADHD (a disorder that is prevalent among young people), has resulted in a corresponding increase in abuse.

By way of illustration, the University of Michigan's Monitoring the Future Survey indicates that 4 percent of high school seniors in the United States abused the drug at least once in the past year. Furthermore, survey of students at a public liberal arts college found that over 50% of survey participants knew other students who had used Ritalin for fun, 16% had used it themselves, and nearly 13% reported their own use included snorting the drug. Although less common, Ritalin is abused among adults as well. Overall, the data suggest that ADHD medication misuse and diversion are common health care problems for stimulant medications, with the prevalence believed to be approximately 5% to 10% of high school students and 5% to 35% of college students, depending on the study. The Drug Enforcement Administration has received reports of Ritalin abuse among diverse segments of the population, ranging from healthcare professionals to street addicts.

Methylphenidate has high potential for abuse due to its pharmacological similarity to cocaine and amphetamines. Methylphenidate, like other stimulants, increases dopamine levels in the brain, but at therapeutic doses this increase is slow, and thus euphoria does not typically occur except in rare instances. The abuse potential is increased when methylphenidate is crushed and insufflated (snorted), or when it is injected, producing effects almost identical to cocaine. Cocaine-like effects can also occur with very large doses taken orally. The dose, however, that produces euphoric effects varies between individuals. Methylphenidate is actually more potent than cocaine in its effect on dopamine transporters. Methylphenidate should not be viewed as a weak stimulant as has previously been hypothesized.

In 2004, over 8000 methylphenidate ingestions were reported in US poison center data. The most common reasons for intentional exposure were drug abuse and suicide attempts. An overdose manifests in agitation, hallucinations, psychosis, lethargy, seizures, tachycardia, dysrhythmias, hypertension, and hyperthermia. Benzodiazepines may be used as treatment if agitation, dystonia, or convulsions are present.

The primary source of methylphenidate for abuse is diversion from legitimate prescriptions, rather than illicit synthesis. Those who use it to stay awake do so by taking it orally, while intranasal and intravenous administration are the preferred means for inducing euphoria. IV users tend to be adults whose use may cause panlobular pulmonary emphysema.

Abuse of prescription stimulants is higher amongst college students than non-college attending young adults. College students use methylphenidate either as a study aid or to stay awake longer. Increased alcohol consumption due to stimulant misuse has additional negative effects on health. Methylphenidate's pharmacological effect on the central nervous system is almost identical to that of cocaine. Studies have shown that the two drugs are nearly indistinguishable when administered intravenously to cocaine addicts.

Patients who have been prescribed RITALIN® have been known to sell their tablets to others who wish to take the drug recreationally. In the USA it is one of the top ten stolen prescription drugs and is known as "kiddie coke", "Vitamin R" and "The R Ball". Recreational users may crush the tablets and either snort the powder, or dissolve the powder in water, filter it through cotton wool into a syringe to remove the inactive ingredients and other particles and inject the drug intravenously. Both of these methods increase bioavailability and produce a much more rapid onset of effects than when taken orally (within approximately 5-10 minutes through insufflation and within just 10-15 seconds through intravenous injection); however the overall duration of action tends to be decreased by any non-oral use of drug preparations made for oral use.

Methylphenidate is sometimes used by students to enhance their mental abilities, improving their concentration and helping them to study. Professor John Harris, an expert in bioethics, has said that it would be unethical to stop healthy people taking the drug. He also argues that it would be "not rational" and against human enhancement to not use the drug to improve people's cognitive abilities. Professor Anjan Chatterjee however has warned that there is a high potential for abuse and may cause serious adverse effects on the heart, meaning that only people with an illness should take the drug. In the British Medical Journal he wrote that it was premature to endorse the use of Ritalin in this way as the effects of the drug on healthy people have not been studied. Professor Barbara Sahakian has argued that the use of Ritalin in this way may give students an unfair advantage in examinations and that as a result universities may have to consider making students give urine samples to be tested for the drug.

Methamphetamine increases alertness, concentration, energy, and in high doses, may induce euphoria, enhance self-esteem and increase libido. Methamphetamine has high potential for abuse and addiction, activating the psychological reward system by triggering a cascading release of dopamine in the brain. Methamphetamine is FDA approved for the treatment of ADHD and exogenous obesity. It is dispensed in the USA under the trademark name DESOXYN®.

Methamphetamine addiction is one of the most difficult forms of addictions to treat.

In addition to their legitimate medical uses, there is a high incidence of illicit use of these stimulants, similarly to the abuse of opioids. However, unlike the case of opioids, direct antagonists to stimulants do not exist and finding competitive non-addictive pharmacological agents is complicated and risky due to side effects.

Stimulants have been abused for both "performance enhancement" and recreational purposes (i.e., to get high). For the former, they suppress appetite (to facilitate weight loss), increase wakefulness, and increase focus and attention.

Some abusers crush the tablets and then snort or inject them. Others dissolve the tablets in water and inject the mixture. Complications from this method of use can arise because insoluble inactive ingredients in the tablets can block small blood vessels. The addiction to stimulants, and their side-effects are of course additional concerns.

The selection of abused stimulants varies from country to country, but the problem is severe everywhere.

"Opioids" are defined as any substance than binds to opioid receptors while "opiates" are the subset of these substances that are derived from opium. Until relatively recently, there was no difference between opioids and opiates because all opioids were derived from opium; however, there are now many entirely synthetic drugs that bind to these receptors. Examples of purely synthetic opioids include fentanyl, and meperidine (DEMEROL®). Examples of opioids derived from opium that are still used in modern medicine are morphine, hydrocodone (in VICODIN®), oxycodone (in OXYCONTIN® and PERCOCET®), and hydromophone (DILAUDID®).

In the context of this invention, "opioids" is meant as any substance than binds to opioid receptors, including opiates, and the actives in the compositions detailed here may be from either natural or synthetic origin.

All opioid drugs may benefit from the novel compositions of this invention. Examples of such opioids are morphine, ethylmorphine, hydromorphone, dihydromorphine, codeine, hydrocodone, oxycodone, butorphanol, buprenorphine, levorphanol, meperidine, alfentanil, remifentanyl, sufentanyl, ethorphine, tapentadol and their mixtures.

Opioids are being abused in much the same way as described above for stimulants. Opiate abuse is both pervasive in American society and difficult to treat. Modern opiates are highly addictive and used for everything from stress relief to pain medication. The modern medicine cabinet, for some, has proven as deadly as any street corner drug dealer.

Solutions have been sought for fighting the negative aspects of the abusive use of opioids. Thus for example, an opiate drug named EMBEDA® (from Alpharma) is marketed in the United States, which contains in addition to the opiate drug morphine also naltrexone. Naltrexone is an opiate antagonist and its role is to counter the effect of the opiate on abusive users, once abused. However, although naltrexone counters the opiate effect, it does not discourage repeated abuse, as it causes no displeasure to the abuser.

There is an unmet need for stimulant or opioid drugs formulated in such a way as to discourage their abuse.

The present invention is directed at providing compositions preventing abusive use of stimulant or opioid drugs and dissuading from future abuse in a safe and effective way.

SUMMARY

In one embodiment, the present invention provides an abuse deterrent oral fixed-dose composition, comprising a stimulant or opioid and an abuse deterrent active, wherein the abuse deterrent active is configured to be bioavailable only when the composition is crushed, ground, or dissolved.

In one embodiment, the abuse deterrent active is a dopamine receptor agonist which activates the dopamine receptor, inducing nausea and/or vomiting, and diminishing the dopamine-induced reward feeling via activation of a positive feedback mechanism, resulting in reduction of dopamine at extracellular level.

In one embodiment, the abuse deterrent active exhibits emetic and/or hyperactivity blocking effects.

In one embodiment, the present invention provides a method of treatment of a patient in need thereof, comprising the administration to the patient of the composition according to some embodiments of the present invention, wherein more than 10% of the abuse deterrent active is bioavailable within the first 24 hrs post administration.

In one embodiment, the present invention provides a method of treatment of a patient in need thereof, comprising the administration to the patient of the composition according to some embodiments of the present invention, wherein more than 2% of the abuse deterrent active is bioavailable prior to the composition being cleared from the patient.

In one embodiment, the present invention provides a method of treatment of a patient in need thereof, comprising the administration to the patient of the composition according to some embodiments of the present invention, wherein more than 1% of the abuse deterrent active is bioavailable prior to the composition being cleared from the patient.

In one embodiment, the present invention provides a method of treatment of a patient in need thereof, comprising the administration to the patient of the composition according to some embodiments of the present invention, wherein less than 10% of the abuse deterrent active is bioavailable within the first 24 hrs post administration.

In one embodiment, the present invention provides a method of treatment of a patient in need thereof, comprising the administration to the patient of the composition according to some embodiments of the present invention, wherein less than 2% of the abuse deterrent active is bioavailable prior to the composition being cleared from the patient.

In one embodiment, the present invention provides a method of treatment of a patient in need thereof, comprising the administration to the patient of the composition according to some embodiments of the present invention, wherein less than 1% of the abuse deterrent active is bioavailable prior to the composition being cleared from the patient.

In one embodiment, the stimulant is selected from the group consisting of metamphetamine, methylphenidate, dexmethylphenidate, methylphenidate derivatives amphetamine, modafinil, and combinations thereof.

In one embodiment, the opioid is selected from the group consisting of: morphine, ethylmorphine, hydromorphone, dihydromorphine, codeine, hydrocodone, oxycodone, butorphanol, buprenorphine, levorphanol, meperidine, alfentanil, remifentanyl, sufentanyl, ethorphine, tapentadol, and combinations thereof.

In one embodiment, the emetic is selected from the group consisting of: apomorphine, ipecac, dopamine receptor agonists, and combinations thereof.

In one embodiment, the abuse deterrent active is apomorphine and the oral fixed dose compositions comprise between 0.5 to 200 mg apomorphine.

In one embodiment, the composition exhibits resistance to alcohol-induced dose dumping of the stimulant.

In one embodiment, the stimulant or the opioid is released in the body in an immediate release or controlled release manner, through a rate controlling polymer layer.

In one embodiment, the composition comprises a core comprising the abuse deterrent active, which is sealed or encapsulated and on top of it is coated a layer comprising the stimulant, which may optionally be coated.

In one embodiment, the composition is formulated as a tablet.

In one embodiment, the composition is formulated as a capsule.

In one embodiment, the composition of the stimulant layer is in a controlled-release form, and the abuse deterrent composition is optionally resistant to alcohol dumping effects.

In one embodiment, the formulation comprises:
a. an abuse deterrent active such as apomorphine layered over sugar spheres;
b. a sealing layer coated over the apomorphine layer, configured to ensure almost no release takes place during at least 36 hrs,
   the sealing layer being configured to resist the dissolution effects in the GI tract by a combination of rate controlling polymers and hydrophilic or hydrophobic plasticizers;
c. a layer comprising a stimulant or opiate coated over the sealing layer;
d. a controlled-release alcohol resistant polymeric layer coated over the stimulant layer, optionally with an inert sub-coating layer,
   wherein the controlled-release alcohol resistant polymeric layer is configured to separate the drug layer from the sealing layer.

In one embodiment, the sealing layer comprises one isolation layer.

In one embodiment, the sealing layer comprises two isolation layers.

In one embodiment, the composition is formulated as a tablet.

In one embodiment, the composition is formulated as a capsule.

In one embodiment, the composition comprises:
a. an abuse deterrent active coated over sugar spheres and then coated with a protective layer;
b. a stimulant or opiate coated over sugar spheres and then coated with a polymeric sustained-release (SR) or extended release (ER) layer; an
c. the two populations of a and b mixed together in an a:b ratio from 20:1 to 1:20 and formulated in a tablet form.

In one embodiment, the composition is formulated as a tablet.

In one embodiment, the composition is formulated as a capsule.

In one embodiment, the present invention provides a kit comprising a composition according to some embodiments of the present invention, and instructions for use.

DETAILED DESCRIPTION

For clarity of disclosure, and not by way of limitation, the detailed description of the invention is divided into the following subsections that describe or illustrate certain features, embodiments or applications of the present invention.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

The present invention provides novel abuse-deterring oral compositions comprising fixed-dose combinations of a stimulant or opioid and an additional active useful as abuse deterrent, formulated in such a way as to liberate the abuse deterrent active only when the oral composition is crushed, ground or dissolved.

Stimulant or opioid drug abusers illicitly use prescription stimulants or opioids, usually by crushing or grinding the prescription tablets and extracting the active with water, and using the extract by injection (such as, for example, by drinking), insufflation or injection.

It was surprisingly found that abusers can be discouraged of illicitly abusing the prescription stimulants or opioids by formulating the stimulant or opioid drugs in a novel oral composition additionally comprising an abuse deterrent active, which will be released only when the oral composition is crushed, ground or dissolved, but not when it is ingested by a patient in the normal course of the medical treatment.

The abusers crushing, grinding, or dissolving the novel oral compositions and extracting the actives will ingest, snort or inject the abuse deterrent active along with the stimulant or opiate and as a result will experience an unpleasant feeling, combined with vomiting. Without intending to be limited to any particular theory, the activation of this positive control loop will cause less deterrant additive to be released, and as a result, the abuser will not only be subjected to the unpleasant effects of the abuse deterrent active, but in addition, will not enjoy the stimulant or opioid effect. As will be shown below, the abuse deterrent active of this invention also exhibits a blocking effect, which further diminishes the stimulant's "reward" effect.

This double effect will dissuade the abusers from repeating the experience, and keep them away from abusing the prescription stimulants. In the alternative routes of abuse like injecting or snorting the emetic effect will be equal or more potent than the withdrawal effects caused by the opioid antagonists, and in addition will have a dissuading effect.

The novel abuse-deterring oral compositions are fixed-dose combinations comprising a stimulant or an opioid and an abuse deterrent active.

The stimulant is selected from the group comprising metamphetamine, methylphenidate, dexmethylphenidate, methylphenidate derivatives amphetamine, modafinil or their mixtures.

The opioid is selected from the group comprising morphine, ethylmorphine, hydromorphone, dihydromorphine, codeine, hydrocodone, oxycodone, butorphanol, buprenorphine, levorphanol, meperidine, alfentanil, remifentanyl, sufentanyl, ethorphine, tapentadol, and their mixtures.

One of the challenges in developing such a combination product is preventing the abuse deterrent active from being released from the composition during normal medical treatment with the stimulant or the opioid, as this could be unpleasant to the patient and impair patient compliance. This challenge was tackled by using novel compositions which protect the abuse deterrent active during the stay of the oral compositions in the body, and only release it on crushing or grinding it, as will be detailed below.

The abuse deterrent active to be used in compositions according to some embodiments of the present invention is selected from the group consisting of: apomorphine, ipecac, and any other entities used as emetics and/or hyperactivity blockers.

In one embodiment, the abuse deterrent active is apomorphine, due to its strong and effective emetic effect, low dose, quick onset and safe use based on its prolonged use in human (APOKIN®) and veterinary applications. Apomorphine does not contain morphine or its chemical skeleton, and does not bind to opioid receptors. It is effective in the treatment of alcoholism, Parkinson's disease and erectile dysfunction.

It has now been surprisingly found that apomorphine, one of the abuse deterrent actives of this invention, in addition to its emetic effect, completely blocks the stimulant's (e.g. Ritalin) induced hyperactivity. Thus, apomorphine exhibits a double effect, an emetic effect causing vomiting and a blocking effect, diminishing the stimulant's "high reward" feeling.

Other dopamine agonists, including L-DOPA, or other compounds having a deterrent effect, based on the activation of the positive feedback mechanism and induction of nausea are suitable for use in the present invention.

In some embodiments, the amount of apomorphine in the composition is between 0.5 mg to 200 mg. In some embodiments, the amount of apomorphine in the composition is 0.5 mg. In some embodiments, the amount of apomorphine in the composition is 1 mg. In some embodiments, the amount of apomorphine in the composition is 2 mg. In some embodiments, the amount of apomorphine in the composition is 3 mg. In some embodiments, the amount of apomorphine in the composition is 4 mg. In some embodiments, the amount of apomorphine in the composition is 5 mg. In some embodiments, the amount of apomorphine in the composition is 6 mg. In some embodiments, the amount of apomorphine in the composition is 7 mg. In some embodiments, the amount of apomorphine in the composition is 8 mg. In some embodiments, the amount of apomorphine in the composition is 9 mg. In some embodiments, the amount of apomorphine in the composition is 10 mg. In some embodiments, the amount of apomorphine in the composition is 11 mg. In some embodiments, the amount of apomorphine in the composition is 12 mg. In some embodiments, the amount of apomorphine in the composition is 13 mg. In some embodiments, the amount of apomorphine in the composition is 14 mg. In some embodiments, the amount of apomorphine in the composition is 15 mg. In some embodiments, the amount of apomorphine in the composition is 16 mg. In some embodiments, the amount of apomorphine in the composition is 17 mg. In some embodiments, the amount of apomorphine in the composition is 18 mg. In some embodiments, the amount of apomorphine in the composition is 19 mg. In some embodiments, the amount of apomorphine in the composition is 20 mg. In some embodiments, the amount of apomorphine in the composition is 40 mg. In some embodiments, the amount of apomorphine in the composition is 60 mg. In some embodiments, the amount of apomorphine in the composition is 80 mg. In some embodiments, the amount of apomorphine in the composition is 100 mg. In some embodiments, the amount of apomorphine in the composition is 150 mg. In some embodiments, the amount of apomorphine in the composition is 200 mg.

In some embodiments, the ratio of stimulant or opiate to deterrent additive is from 1:100 to 100:1. In some embodiments, the ratio of stimulant or opiate to deterrent additive is 1:100. In some embodiments, the ratio of stimulant or opiate to deterrent additive is 2:100. In some embodiments, the ratio of stimulant or opiate to deterrent additive is 4:100. In some embodiments, the ratio of stimulant or opiate to deterrent additive is 6:100. In some embodiments, the ratio of stimulant or opiate to deterrent additive is 8:100. In some embodiments, the ratio of stimulant or opiate to deterrent additive is 10:100. In some embodiments, the ratio of stimulant or opiate to deterrent additive is 20:100. In some embodiments, the ratio of stimulant or opiate to deterrent additive is 40:100. In some embodiments, the ratio of stimulant or opiate to deterrent additive is 60:100. In some embodiments, the ratio of stimulant or opiate to deterrent additive is 80:100. In some embodiments, the ratio of stimulant or opiate to deterrent additive is 1:1. In some embodiments, the ratio of stimulant or opiate to deterrent additive is 100:80. In some embodiments, the ratio of stimulant or opiate to deterrent additive is 100:60. In some embodiments, the ratio of stimulant or opiate to deterrent additive is 100:40. In some embodiments, the ratio of stimulant or opiate to deterrent additive is 100:20. In some embodiments, the ratio of stimulant or opiate to deterrent additive is 100:10. In some embodiments, the ratio of stimulant or opiate to deterrent additive is 100:8. In some embodiments, the ratio of stimulant or opiate to deterrent additive is 100:6. In some embodiments, the ratio of stimulant or opiate to deterrent additive is 100:4. In some embodiments, the ratio of stimulant or opiate to deterrent additive is 100:2. In some embodiments, the ratio of stimulant or opiate to deterrent additive is 100:1.

Administration of RITALIN® (methylphenidate HCl—Novartis) to mice increases their activity (hyperactivity), processes, known to be modulated via dopamine release.

While not bound by a specific theory, apomorphine significantly reduces the release of dopamine and the extracellular levels of dopamine metabolites, DOPAC and HVA, not only in the striatum, but also in the prefrontal cortex, which seems to indicate that dopamine autoreceptors modulate in vivo release of dopamine in the prefrontal cortex. Apomorphine (a dopamine non-selective receptor agonist) markedly reduces dopamine baseline activity presumably via activation of dopamine autoreceptor (pre and/or post synaptic receptors).

In one embodiment, the present invention provides compositions comprising a stimulant or opioid and an abuse deterrent active which activates the dopamine receptor, inducing vomiting and diminishing the dopamine-induced reward feeling via reduction of dopamine at extracellular level (pre and/or post synaptic receptors).

A pilot study in mice of the apomorphine mediated inhibition (blocking) of RITALIN®-induced hyperactivity in activity box was carried out (Example 5). The study examined the effect of co-administration of both RITALIN® and apomorphine in mice on the motor activity assessed in the activity box. Male mice C57BI weighing about 22 g were used in the study.

Treatment with 8 mg/kg RITALIN® induced hyperactivity which manifested by extended move time and distance covered. Apomorphine, on the other hand, caused a sudden ataxia in animals, with nearly still locomotion. The move coordinated by the animal included an oscillation like movement with little covered distance, Injection of apomorphine five minutes after RITALIN® administration, totally abolished the effect of RITALIN®, and animals looked nearly ataxic with little movement. Entering the vertical plan was also abolished by apomorphine.

Discussion and Conclusion

At the current dosage regimen in which apomorphine was given at 5 mg/kg and RITALIN® at 8 mg/kg, the results were unequivocally clear that RITALIN® acts as a stimulant and induces hyperactivity in mice, whereas apomorphine induces hypoactivity and nearly ataxic behavior. The combination of both, although RITALIN® was given 5 min prior to apomorphine, still resulted in total dominance of the effect induced by apomorphine over that induced by RITALIN®; meaning that animals behaved as if they were injected with apomorphine alone.

In a second study (Example 6), apomorphine and RITALIN® were administered to mice at human equivalent dosing of 6 and 40 mg per 60 Kg human body weight respectively. The dosing administered to mice (n=4) was 1.23 mg/Kg apomorphine and 8.25 mg/Kg RITALIN®.

Also in this second study, the observation of the animals post RITALIN® administration shows a drastic increase in the animals' activity. The injection of apomorphine dramatically decreased the animals movement, and thus subdued the Ritalin®-induced hyperactivity.

Thus, it was surprisingly found that apomorphine inhibits or blocks the RITALIN®-induced hyperactivity. It was not previously known whether apomorphine has a blocking effect on RITALIN®-mediated hyperactivity.

Both the emetic and the blocking effect work together towards dissuading abusers from abusing prescription stimulants.

In one embodiment, the present invention provides abuse deterrent fixed dose combinations comprising a stimulant or opioid and an abuse deterrent active exhibiting emetic and/or hyperactivity blocking effects.

In one embodiment, the abuse deterrent active of this invention is apomorphine.

The abuse deterrent active in compositions according to some embodiments of the present invention will be properly protected by encapsulation, coating or other means, which will ensure that most or all of it in the compositions will not be released during the stay of the composition in the gastro-intestinal tract and will be excreted as such. On the other hand, once the abuser will grind, crush, or somehow extract the novel oral compositions, the abuse deterrent active will be extracted together with the stimulant or opiate and when used by injection, snorting, drinking, etc., an unpleasant feeling combined with vomiting will take place, discouraging the abuser from further use.

In one embodiment, the novel oral compositions may be in tablet form, having a core comprising the abuse deterrent active, which is sealed or encapsulated and on top of it is coated a layer comprising the stimulant, which may optionally be coated. The composition of the stimulant layer is preferably in controlled-release form. In addition, the abuse deterrent composition is optionally resistant to alcohol dumping effects.

In one embodiment, the novel oral compositions may be in capsule form, which capsules may be filled with particles comprising:

a. an abuse deterrent active such as apomorphine layered over sugar spheres (also known as non-pareil or NP)

b. a unique and robust sealing layer coated over the apomorphine layer, ensuring almost no release takes place during at least 36 hrs. This layer will be robust enough to resist the dissolution effects in the GI tract due to a unique combination of rate controlling polymers and hydrophilic or hydrophobic plasticizers which might be layered in one or two separate isolation layers.

c. a layer comprising a stimulant or opiate coated over the sealing layer.

d. a controlled-release alcohol resistant polymeric layer coated over the stimulant layer, optionally with an inert sub-coating layer (separating the drug layer from the sealing layer).

In some embodiments, the novel compositions comprise two coated beads or sugar spheres populations:

a. An emetic coated over sugar spheres (non-pareils) and then coated with a protective layer b. A stimulant or opiate coated over sugar spheres and then coated with a polymeric sustained-release (SR) or extended release (ER) layer.

c. The two beads populations are then mixed together in an a:b ratio from 20:1 to 1:20, and formulated in a tablet form.

In some embodiments, the composition is formulated as a capsule.

In some embodiments, the a:b ratio is 20:1. In some embodiments, the a:b ratio is 10:1. In some embodiments, the a:b ratio is 5:1. In some embodiments, the a:b ratio is 2:1. In some embodiments, the a:b ratio is 1:1. In some embodiments, the a:b ratio is 1:5. In some embodiments, the a:b ratio is 1:10. In some embodiments, the a:b ratio is 1:20.

While the three compositions detailed above are preferred compositions, it will be evident to one skilled in the art that other compositions known in the art, such as double layer tablets, suspensions with the two types of beads, etc. may be used to implement the basic ideas of the present invention.

Reference is now made to the following examples, which together with the above descriptions illustrate some embodiments of the invention in a non-limiting fashion.

EXAMPLES

Example 1

Stimulant and Abuse Deterrent Active Fixed-Dose Combination—Core Coated Composition

Apomorphine Core:
  Mix 100 g apomorphine HCl together with 300 g Avicel PH 200 and 10 g PVP K30, add water and granulate.
  Screen through 0.8 mesh and add 5 g magnesium stearate.
  Mix 3 minutes and compress tablets containing 10 mg apomorphine each.
  Coat the tablets with a 10% w/w layer of Eudragit RS/RL (90:10) and TEC/DBS 5% of the dry polymer.
  An additional 5% w/w layer of Ethocel 50cp with 5% DBS as plasticizer is coated over the Eudragit layer.
  Methylphenidate (30 mg/tab) together with PVP k30 5% as binder is coated over the Ethocel layer.
  10% w/w of polymeric layer-Ethocel 20 cp with 10% TEC is coated over the methylphenidate layer.

Example 2

Stimulant and Abuse Deterrent Active Fixed-Dose Combination—One Population of Beads

Stage 1:
  Take 500 g of sugar beads, NP's 25/30;
  Prepare coating solution with 50 g apomorphine HCl together with 5 g PVP K90, dissolved in 300 g ethanol/water 50:50 solution;
  Coat the NP's with the apomorphine by using a fluid bed equipped with Wurster column (bottom spraying).
Stage 2:
  Coat a layer of cellulose acetate (CA), 20% w/w with 5% PEG 6000 as plasticizer (emetic-isolating layer).
Stage 3:
  On the CA layer coat methylphenidate in a ratio of methylphenidate/apomorphine of 2:1. The methylphenidate mixed with PVP K30 as binder (100 g:5 g respectively) will be coated by using fluid bed equipped with Wurster.
Stage 4:
  Coat the methylphenidate layer with an external layer of ethyl cellulose 45 cp, 10% w/w with 10% w/w of DBS (release rate controlling layer);
  Fill size 1 or 0 hard gelatin capsules with beads comprising 10 mg of apomorphine and 20 mg methylphenidate.

Example 3

Opioid and Abuse Deterrent Active Fixed-Dose Combination—One Population of Beads

Stage 1:
  Weigh 500 g of sugar beads, NP's 25/30;
  Prepare coating solution with 50 g apomorphine HCL together with 5 g PVP K90, dissolved in 300 g ethanol/water 50:50 solution;
  Coat the NP's with the apomorphine by using a fluid bed equipped with Wurster column (bottom spraying).
Stage 2:
  Coat a layer of cellulose acetate (CA), 20% w/w with 5% PEG 6000 as plasticizer (emetic-isolating layer).
Stage 3:
  On the CA layer coat methylphenidate in a ratio of methylphenidate/apomorphine of 5:1. The methylphenidate mixed with PVP K30 as binder (250 g:25 g respectively) will be coated by using a fluid bed equipped with Wurster;
  Fill size 1 or 0 hard gelatin capsules with beads comprising 10 mg of apomorphine and 50 mg methylphenidate.

Example 4

Stimulant and Abuse Deterrent Active Fixed-Dose Combination—Two Bead Populations

Stage 1:
  Weigh 500 g of sugar beads, NP's 25/30;
  Prepare coating solution with 50 g apomorphine HCl together with 5 g PVP K90, dissolved in 300 g ethanol/water 50:50 solution;
  Coat the NP's with the apomorphine by using a fluid bed equipped with Wurster column (bottom spraying).
Stage 2:
  Coat a layer of cellulose acetate (CA), 20% w/w with 5% PEG 6000 as plasticizer (emetic-isolating layer).
Stage 3:
  Separate population of methylphenidate beads: on NP's 25/30 coat methylphenidate in a ratio of methylphenidate/NP's of 1:1. The methylphenidate mixed with PVP K30 as binder (200 g:10 g respectively) will be coated by using fluid bed equipped with Wurster.
Stage 4:
  Coat the methylphenidate layer with external layer of Ethyl cellulose 45 cp, 10% w/w with 10% w/w of DBS (release rate controlling layer);
  Fill size 1 or 0 hard gelatin capsules with beads mixed from the two groups comprising 10 mg of apomorphine beads and 20 mg methylphenidate beads.

Example 5

Apomorphine Mediated Inhibition of RITALIN®-Induced Hyperactivity in Activity Box

A pilot study in mice of the apomorphine mediated inhibition of Ritalin®-induced hyperactivity in activity box was carried out. The study examined the effect of co-administration of both RITALIN® and apomorphine in mice on the motor activity assessed in the activity box. Male C57BI mice weighing about 22 g were used in the study.

Mice were administered saline solutions of the two actives as follows:

Methylphenidate was dissolved in saline 0.9% to a concentration of 0.5 mg/ml,

Apomorphine was dissolved in saline 0.9% to a concentration of 0.8 mg/ml.

Both compounds' solutions were administered at dose volume of 10 mg/kg.

Motor Activity Assessment

Animals' motor locomotion in four groups (1-4 M) was assessed in the activity box. Animals were placed in the activity box and several parameters were observed including movement time, distance, V-plan entries, margin vs. center time, and other parameters. Groups 1-3 M were monitored for 30 minutes each, during which all parameters were assessed at 2 minutes intervals. In the 4 M group, animals were monitored for 60 minutes with 2 minutes assessment intervals. The assessment in the activity box was done in total darkness (red light was used for illumination). The main parameters that were calculated in this study were the move time, total distance and vertical plan entry. The observation for groups 1-3 M were made during 30 minutes with 2 minutes calculation intervals of each parameter. In the fourth group (4 M) the observations were extended for 60 minutes with 2 minutes calculation intervals Treatment with 5 mg/kg RITALIN® induced hyperactivity which manifested by extended move time and distance. The naïve animals showed a decline move time and consequently covered distance over time, emphasizing accustoming to the new arena and decline in the explorative move. There was no significant change over time in the RITALIN® induced group.

Apomorphine, on the other hand caused a sudden ataxia in animals, with nearly still locomotion. The move coordinated by the animal included an oscillation like movement with little covered distance. Injection of apomorphine 5 minutes after RITALIN® administration, totally abolished the effect of RITALIN®, and animals looked nearly ataxic with little movement. Entering the vertical plan was also abolished by apomorphine, Discussion and Conclusion At the current dosage regimen in which apomorphine was given at 5 mg/kg and Ritalin® at 8 mg/kg, the results were unequivocally clear that RITALIN® acts as a stimulant and induces hyperactivity in mice, whereas apomorphine induces hypoactivity and nearly ataxic behavior. The combination of both, although RITALIN® was given 5 min prior to apomorphine, still resulted in total dominance of the effect induced by apomorphine over that induced by Ritalin®; meaning animals behaved as if they were injected with apomorphine alone.

Example 6

Apomorphine Inhibition (Blocking) of the Hyperactivity Ritalin®-Induced Effect when Administered at Human Equivalent Dosing of 6 and 40 Mg Per 60 Kg Human Weight, Respectively In a second study, apomorphine and RITALIN® were administered to mice at human equivalent dosing of 6 and 40 mg per 60 Kg human body weight respectively. The dosage administered to mice (n=4) was 1.23 mg/Kg apomorphine and 8.25 mg/Kg RITALIN®. Also in this second study, the observation of the animals post RITALIN® administration shows a drastic increase in the animals' activity. The injection of apomorphine dramatically decreased the animals movement, and thus subdued the RITALIN®-induced hyperactivity.

Example 7

Figure 1:
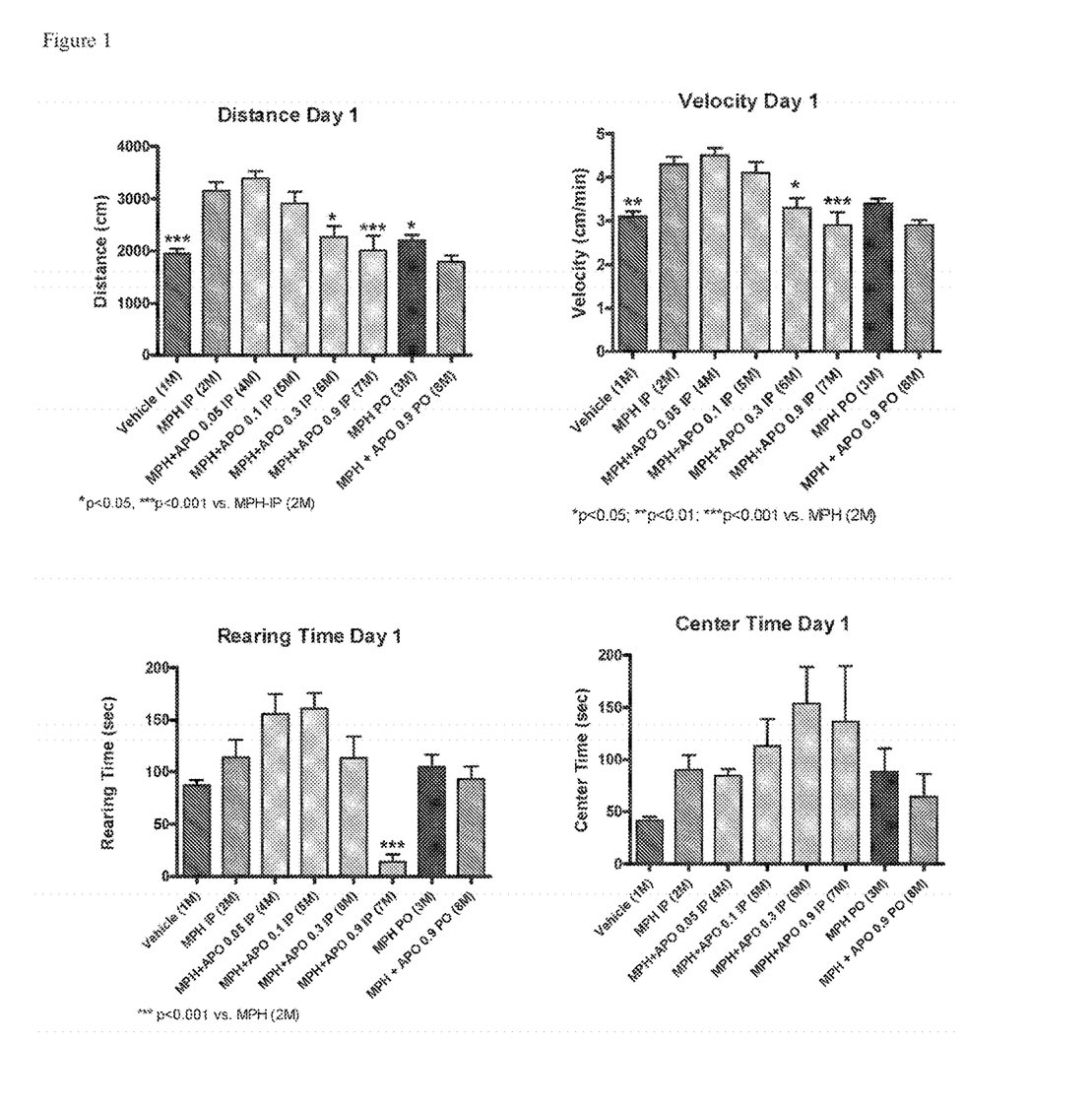
FIG. 1 shows the open field test results from mice treated according to some embodiments of the present invention.

Dose response and Behavioral Study with Methylphenidate and Apomorphine and Their Combination in Mice Summary Eight groups comprising eight or nine C57bl/6J male mice were assigned for this study. Methylphenidate (MPH) was used as the model inducer. One reference group received Vehicle administered IP (1M), two groups received Methylphenidate (5 mg/kg) alone, administered IP (2M) or PO (3M), and five groups received combined formulation of Methylphenidate (5 mg/kg) and Apomorphine 0.05 mg/kg IP (4M), 0.1 mk/kg IP (5M), 0.3 mg/kg IP (6M), 0.9 mg/kg IP (7M) and 0.9 mg/kg PO (8M). Spontaneous activity in Open Field Test (OFT) was performed. The results are shown in FIG. 1.

Methylphenidate IP (2M) treatment significantly increased distance travelled and velocity on Day 1 compared to Vehicle-treated controls (1M). Combination with Apomorphine 0.3 mk/kg IP (6M) and 0.9 mg/kg IP (7M) significantly reduced these effects in a dose dependent manner. Apomorphine 0.9 mg/kg IP in combination with Methylphenidate (7M) significantly reduced rearing time.

These results indicate that Methylphenidate caused elevation in locomotor activity, and Apomorphine antagonized this effect in a dose-dependent manner.

Experimental Model

Each Test Item and vehicle formulation was administrated to 8/9 mice per group. The administration was performed PO or IP according to group allocation in Table 1.

TABLE 1

Group Allocation

| Group No. | Treatment (mg/kg) | No. of Animals | Animals ID | Dose Volume (ml/kg) | ROA |
|---|---|---|---|---|---|
| 1M | Vehicle (0) | 8 | 1, 2, 18, 19, 35, 36, 52, 53 | 10 | IP |
| 2M | Methylphenidate (5) | 8 | 3, 4, 20, 21, 37, 38, 54, 55 | | IP |
| 3M | Methylphenidate (5) | 8 | 5, 6, 22, 23, 39, 40, 56, 57 | | PO |
| 4M | Methylphenidate (5) + Apomorphine (0.05) | 8 | 7, 8, 41, 42, 43, 58, 59, 60 | | IP |
| 5M | Methylphenidate (5) + Apomorphine (0.1) | 8 | 9, 10, 26, 27, 44, 45, 61, 62 | | |
| 6M | Methylphenidate (5) + Apomorphine (0.3) | 8 | 11, 12, 28, 29, 46, 47, 63, 64 | | |
| 7M | Methylphenidate (5) + Apomorphine (0.9) | 9 | 13, 14, 30, 31, 34, 48, 49, 65, 66 | | |
| 8M | Methylphenidate (5) + Apomorphine (0.9) | 8 | 15, 16, 32, 33, 50, 51, 67, 68 | | PO |

Open Field Test (OFT)

The open field test (OFT) is a commonly used qualitative and quantitative measure of general locomotor activity and willingness to explore in rodents. Open Field test (OFT) was performed according to Pharmaseed SOP No. 113: "Open Field for Mice Testing". OFT was performed 15 or 30 min after test item IP or PO administration, respectively.

Fifteen minutes after test item/vehicle administration, mice were placed at the center of an open field box (43× 43×40 cm) approximately at the same time of the day. On each side of the open field box, two frames placed at 2 and 5 cm height with 16 photocell beams per side ensured movement detection. The computer defined grid lines that divided the open field into two compartments: margin and center. Several variables were recorded during a 15 minute session of spontaneous activity including:

- Indices of motor exploratory activity: distance travelled, moving time, and velocity
- Indices of habituation: distance travelled during the last 5-min period in percent of the first+last 5-min periods.
- Indices of anxiety: percentage of distance travelled and time spent in the central zone of the open-field.
- Curiosity activity: rearing episodes and time Open Field Test (Activity Box)

OFT was performed 15 or 30 min after test item IP or PO administration, respectively. The parameters measured were distance and velocity as indicators of general motility, time spent in center as an indicator for anxiety and rearing time as indicator of the animal's curiosity. On Day 1, Methylphenidate IP (2M) treatment significantly increased distance travelled and velocity compared to Vehicle-treated controls (1M) as shown in FIG. 1 and Table 2. Combination with Apomorphine 0.3 mk/kg IP (6M) and 0.9 mg/kg IP (7M) significantly reduced these effects in a dose dependent manner. Apomorphine 0.9 mg/kg IP in combination with Methylphenidate (7M) significantly reduced rearing time on Day 1 compared to Methylphenidate IP treated group (2M).

In order to access the effect of habituation, we calculated the percent of distance travelled during the last five minutes out of cumulative distance travelled during the first and the last five minutes. Whereas on Day 1 there were no differences between the first and the last five minutes indicating on habituation to the Open Field apparatus.

TABLE 2

Group Average of AB Parameters on Day 1

| | Distance (cm) | SEM | Velocity (cm/sec) | SEM | Rearing Time (sec) | SEM | N | Center Time (sec) | N | SEM |
|---|---|---|---|---|---|---|---|---|---|---|
| Vehicle (1M) | 1948.1*** | 93.8 | 3.1* | 0.1 | 87.1 | 5.1 | 8 | 41.5 | 6 | 3.6 |
| MPH IP (2M) | 3147.1 | 168.7 | 4.3 | 0.2 | 114.3 | 16.7 | 8 | 89.8 | 6 | 14.8 |
| MPH + APO 0.05 IP (4M) | 3381.2 | 141.0 | 4.5 | 0.2 | 155.6 | 19.3 | 8 | 84.3 | 6 | 6.2 |
| MPH + APO 0.1 IP (5M) | 2911.2 | 222.7 | 4.1 | 0.2 | 160.8 | 14.7 | 8 | 113.3 | 6 | 25.8 |
| MPH + APO 0.3 IP (6M) | 2273.9* | 199.8 | 3.3* | 0.2 | 113.5 | 20.8 | 8 | 153.7 | 6 | 35.0 |
| MPH + APO 0.9 IP (7M) | 2013.2*** | 278.5 | 2.9*** | 0.3 | 14.1*** | 7.0 | 9 | 136.4 | 7 | 53.2 |
| MPH PO (3M) | 2198.4* | 110.4 | 3.4 | 0.1 | 104.5 | 12.2 | 8 | 88.2 | 6 | 22.6 |
| MPH + APO 0.9 PO (8M) | 1794.1 | 125.4 | 2.9 | 0.1 | 93.0 | 12.1 | 8 | 64.3 | 6 | 21.6 |

*p < 0.05,
***p < 0.001 vs. Methylphenidate IP (2M)

Discussion

Methylphenidate IP (2M) treatment significantly increased distance travelled and velocity on Day 1 compared to Vehicle-treated controls (1M) in Open Field (OFT) paradigm. Combination with Apomorphine 0.3 mk/kg IP (6M) and 0.9 mg/kg IP (7M) significantly reduced these effects in a dose dependent manner. Apomorphine 0.9 mg/kg IP in combination with Methylphenidate (7M) significantly reduced rearing time on Day 1 compared to Methylphenidate IP treated group (2M).

Example 8

PK/PD Study with Methylphenidate and Apomorphine Administered Alone or in Combination in Dogs Summary Behavioral effects and pharmacokinetic profile of Methylphenidate and Apomorphine and their combinations were assessed in dogs.

Six groups comprising six dogs were assigned for this Example. Methylphenidate (MPH) was used as the model inducer. Two groups received Methylphenidate alone, administered IV (1.7 mg/kg—group 1) or PO (0.3 mg/kg—group 2), two groups received Apomorphine alone, administered IV (0.15 mg/kg—group 3) or PO (0.027 mg/kg—group 4) and two groups received the same dose levels of the combined formulation of Methylphenidate and Apomorphine, IV (group 5) or PO (group 6). Behavioral observation was performed during 6 hours following test items administration and blood samples were taken on 4 dogs per group at 0.25, 0.5, 1, 1.5, 3, 4 and 6 hours post-administration for pharmacokinetic (PK) analysis.

The results indicated that Methylphenidate IV caused increased activity levels in dogs and Apomorphine, besides inducing emesis, diminished the observed increases in activity. Moreover, PK analysis revealed no substantial pharmacokinetic interaction between the two tested drugs.

Methods

Animals: Mixed breed dogs (5 Males+7 females/12/3 to 5 years/10.5 to 18.5 kg, from SPM Biocameltec) were used in the studies outlined in this example.

Administration of the test items: Each Test Item was administrated to 6 dogs per group. The administration was performed PO or IV according to group allocation in Table 3. The study was performed in 3 cycles and a period of wash-out of at least 10 days was respected between each cycle.

TABLE 3

Group Allocation

| Group No. | n = | Treatment | Dose Level (mg/kg) | ROA | Dose volume | Conc. (mg/ml) |
|---|---|---|---|---|---|---|
| 1 | 6 | Methylphenidate | 1.7 | IV | 1 ml/kg | 1.7 |
| 2 | 6 | Methylphenidate | 0.3 | PO | — | — |
| 3 | 6 | Apomorphine | 0.15 | IV | 1 ml/kg | 0.15 |
| 4 | 6 | Apomorphine | 0.027 | PO | — | — |
| 5 | 6 | Methylphenidate + apomorphine | 1.7 + 0.15 | IV | 1 ml/kg | 1.7 + 0.15 |
| 6 | 6 | Methylphenidate + apomorphine | 0.3 + 0.027 | PO | — | — |

Behavior observation: The animals were observed every 10 minutes during the first 2 hours post administration, and every 20 minutes thereafter, for 6 hours. Observations included respiratory, circulatory, autonomic and central nervous systems, somatomotor activity and behavior pattern (e.g. sedation, respiration rate, changes in mentation, gait, and the like). In particular, induction of emesis (for dogs administered with apomorphine) and hyperactivity (for dogs administered with methylphenidate) were recorded. To measure activity levels, two scales were followed as presented in Table 4 and Table 5.

TABLE 4

Scoring Table to Define Dog Activity During the Test - General Scoring and Clinical Observations by a Veterinarian

| Activity | Score |
|---|---|
| very active | 4 |
| active | 3 |
| normal | 2 |
| not very active | 1 |
| sedative | 0 |
| Per any additional observation (clinical signs) | +1 |

TABLE 5

Scoring Table to Define Dog Activity During the Test - Video Observation

| Activity | Score |
|---|---|
| barking | +2 |
| jumping | +2 |
| Walking/circling | +1 |
| polypnea | +2 |
| hallucination | +3 |
| Increased Somatomotor activity | +2 |

TABLE 5-continued

Scoring Table to Define Dog Activity During the Test - Video Observation

| Activity | Score |
|---|---|
| Very dynamic | +2 |
| dynamic | +1 |
| Less dynamic | +0.5 |
| normal | +1 |
| Tired-seated | +0.5 |

Blood Collection and PK analysis: For blood collection, a 5 ml syringe was used and blood sampling was directly collected at the jugular vein. Blood samples were collected in K3-EDTA tubes at the following time points: 0.25, 0.5, 1, 1.5, 3, 4 and 6 hours post-administration (7 samples). At each time point, 6 ml of blood was collected for 4 drug-treated dogs. Plasma samples were analyzed using LC-MS/MS and PK analysis was performed using the PK Solutions Version 2.0 program.

Results

Emesis: Apomorphine is an opioid drug that acts as a potent central dopamine agonist to directly stimulate the chemoreceptor trigger zone in the area postrema. It can be administered PO (greater than 4 mg/kg), IV (greater than 0.02 mg/kg) or SC (greater than 0.3 mg/kg) to induce vomiting in dogs. As expected, apomorphine administered PO at the dose of 0.027 mg/kg (group 4) did not induce emesis. However, for dogs injected IV with 0.15 mg/kg apomorphine (group 3 and group 5), apomorphine-induced emesis was observed in all treated dogs within 1-2 minutes post administration. The time to induce vomiting was recorded. As shown in Table 6, the mean time to induce emesis was the same for the group administered with Apomorphine alone (group 3) and for the group administered with apomorphine+MPH (group 5).

TABLE 5

Recorded time for observed emesis following apomorphine administration (minutes)

| | Group | | | |
|---|---|---|---|---|
| | #3 Apo IV | #4 Apo PO | #5 MPH + Apo IV | #6 MPH + Apo PO |
| Dog 1 | 0.9 | — | 0.7 | — |
| Dog 2 | 1.0 | — | 0.9 | — |
| Dog 3 | 1.5 | — | 1 | — |
| Dog 4 | 1.1 | — | 1.1 | — |
| Dog 5 | 0.8 | — | 1.1 | — |
| Dog 6 | 1.1 | — | 1.2 | — |
| Mean | 1.1 | — | 1.0 | — |
| SD | 0.2 | — | 0.2 | — |

Figure 2:
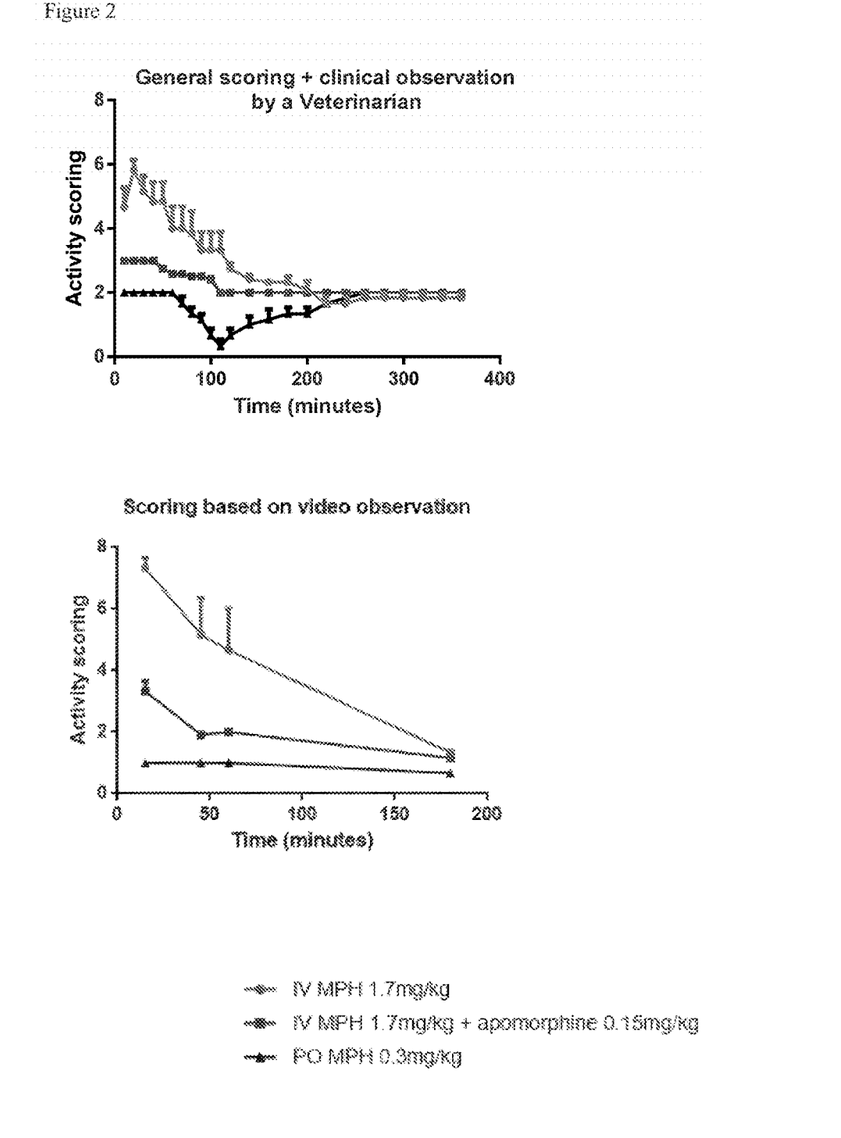
FIG. 2 shows the observed activity levels in dogs treated according to some embodiments of the present invention.

Hyperactivity: As shown in FIG. 2, Methylphenidate PO treatment (group 2) did not induce significant modification of activity levels, with an attributed score corresponding to "normal" dogs. However, MPH IV treatment (group 1) significantly increased dog activity levels, notably during the first 60-100 min. Combination with Apomorphine 0.15 mg/kg IV (group 5) significantly reduced the observed increase in activity.

Some specific clinical signs related to MPH treatment (group 1) was observed, such as polypnea (6 dogs/6), increased somatomotor activity (6 dogs/6), and hallucination (1 dog/6). These clinical signs were observed during at least the 30 first minutes post administration, until 50-70 minutes, and up to 110 minutes in one dog.

Interestingly, these specific clinical signs were not observed when apomorphine was administered concomitantly with MPH (group 5), indicating that apomorphine treatment abolished these MPH-induced clinical signs. Moreover, video observation revealed different behavior associated to hyperactivity between groups during the first 60-100 min with constant barking, jumping, walking/circling and a very dynamic state in dogs from group 1, while some dogs from group 5 were found only with circling episodes.

Figure 3:
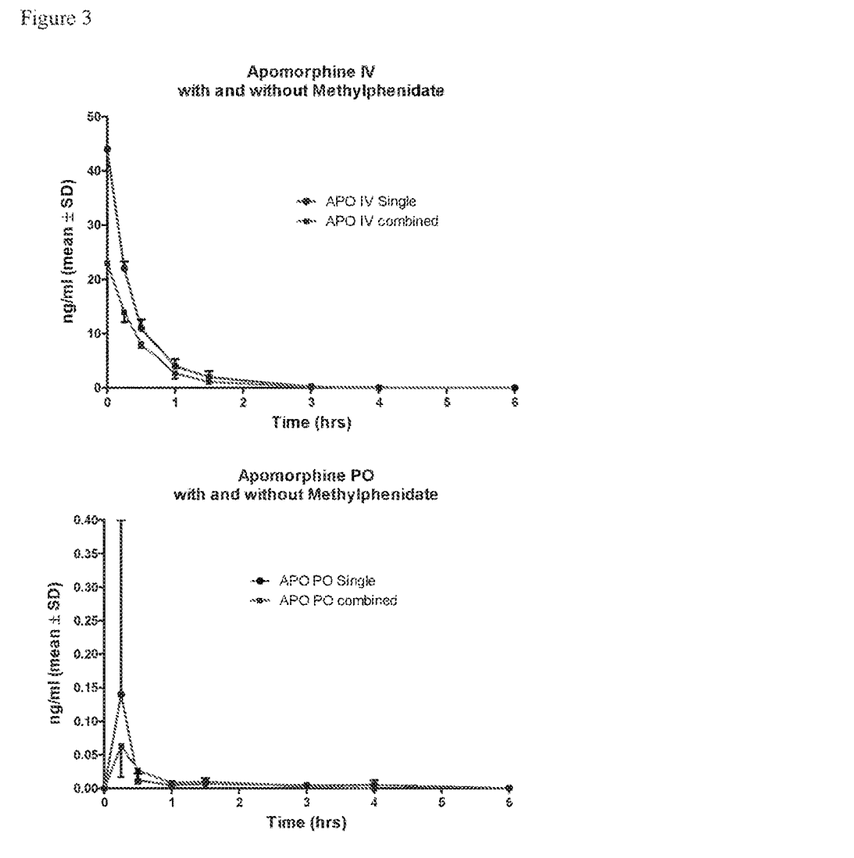
FIG. 3 shows the pharmacokinetic profile of apomorphine according to some embodiments of the present invention.

PK analysis: The objective of the PK analysis was to reveal any possible interaction between the two tested drugs, in relation to their PK parameters. The profiles for Apomorphine concentrations in dogs' plasma following IV and PO administration, with and without Methylphenidate, are shown in FIG. 3.

Apomorphine plasma levels revealed low levels in dogs' plasma, especially following oral administration, resulting in low calculated bioavailability.

Figure 4:
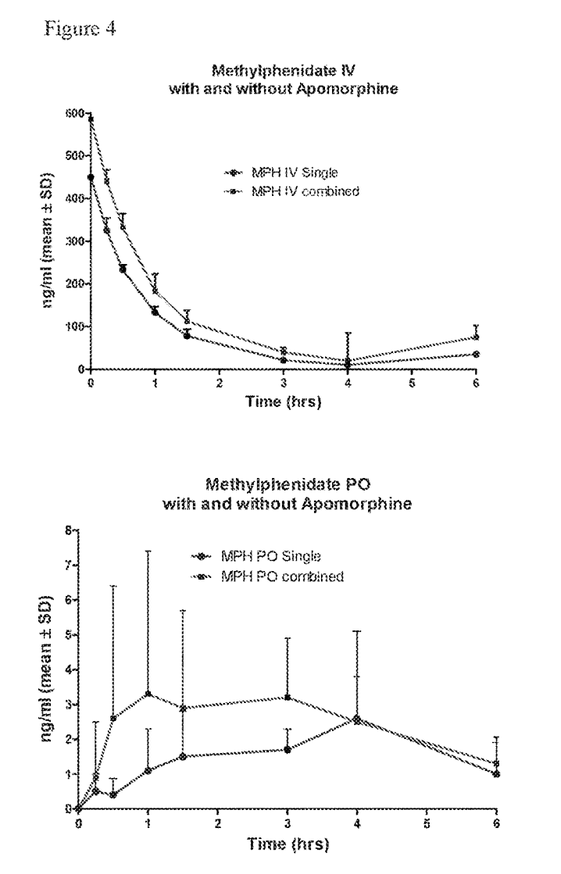
FIG. 4 shows the pharmacokinetic profile of methylphenidate according to some embodiments of the present invention.

The profiles for Methylphenidate concentrations in dogs' plasma following IV and PO administration, with and without Apomorphine, are shown in FIG. 4.

The bioavailability of Methylphenidate was comparable to values published previously in the literature and was not affected by the co-administration of Apomorphine.

Co-administration of Apomorphine and Methylphenidate led to slight changes in the PK profiles (somewhat lower values for Apomorphine and somewhat higher values for Methylphendate), however t-test analysis revealed that these changes had no statistical significance.

Discussion

Behavior observation results revealed that Methylphenidate IV treatment induced increased activity levels in dogs and combination with Apomorphine 0.15 mg/kg IV significantly reduced these effects as well as inducing emesis.

PK analysis results revealed that the bioavailability of Methylphenidate or any other PK parameters were not affected by the co-administration of Apomorphine.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. An abuse deterrent oral fixed-dose composition, comprising a stimulant and an abuse deterrent active, wherein the abuse deterrent active is configured to be bioavailable only when the composition is crushed, ground, or dissolved for a non-oral administration,
   wherein the abuse deterrent active exhibits both emetic effect and hyperactivity blocking effect in said non-oral administration,
   wherein the stimulant is methylphenidate and the abuse deterrent active is apomorphine,
   wherein the oral fixed-dose composition comprises between 0.5 to 200 mg apomorphine,
   wherein the oral fixed-dose composition comprises an effective apomorphine/methylphenidate ratio so that when the composition is crushed, ground or dissolved for said non-oral administration the oral fixed-dose composition does not induce ataxia, and
   wherein the apomorphine/methylphenidate ratio ranges from 0.045 to 0.18.

2. The composition of claim 1, wherein the composition exhibits resistance to alcohol-induced dose dumping of the stimulant.

3. The composition of claim 1, wherein the stimulant is released in the body in an immediate release or controlled release manner, through a rate controlling polymer layer.

4. The composition of claim 1, wherein the apomorphine is administered in a dose lower than 5 mg/kg when the composition is non-orally administered.

5. The composition of claim 1, wherein the composition comprises a core comprising the abuse deterrent active, which is sealed or encapsulated, and a layer comprising the stimulant coating the core.

6. The composition of claim 5, wherein the composition is formulated as a tablet or a capsule.

7. The composition of claim 5 further comprising a coat coating the layer comprising the stimulant.

8. The composition of claim 5, wherein the composition of the stimulant layer is in a controlled-release form.

9. The composition of claim 8, wherein the composition is resistant to alcohol-induced dose dumping effects.

10. A kit comprising a composition of claim 1 and instructions for use.

11. A method of treatment of a patient in need thereof, comprising the administration to the patient of the composition of claim 1, wherein less than 10% of the abuse deterrent active is bioavailable within the first 24 hrs post administration.

12. An abuse deterrent oral fixed-dose composition, comprising a stimulant and an abuse deterrent active, wherein the abuse deterrent active is configured to be bioavailable only when the composition is crushed, ground, or dissolved for a non-oral administration,
   wherein the abuse deterrent active exhibits both emetic effect and hyperactivity blocking effect in said non-oral administration,
   wherein the stimulant is methylphenidate and the abuse deterrent active is apomorphine,
   wherein the oral fixed-dose composition comprises between 0.5 to 200 mg apomorphine,
   wherein the oral fixed-dose composition comprises an effective apomorphine/methylphenidate ratio so that when the composition is crushed, ground or dissolved for said non-oral administration the oral fixed-dose composition does not induce ataxia, and
   wherein the apomorphine/methylphenidate ratio ranges from 0.06 to 0.18.

13. An abuse deterrent oral fixed-dose composition, wherein the composition comprises:
   a. an abuse deterrent active coated over sugar spheres and then coated with a protective layer;
   b. a stimulant coated over sugar spheres and then coated with a polymeric sustained-release (SR) or extended release (ER) layer; and
   c. the two populations of a and b mixed together in an a:b ratio from 20:1 to 1:20 and formulated in a tablet form.

* * * * *